(12) United States Patent
Diehl et al.

(10) Patent No.: US 8,217,217 B2
(45) Date of Patent: *Jul. 10, 2012

(54) ABSORBENT ARTICLE HAVING A DEHYDRATION INDICATOR

(75) Inventors: Joseph Raymond Diehl, Hamilton, OH (US); Donald Carroll Roe, West Chester, OH (US); Patrick Jay Allen, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 248 days.

This patent is subject to a terminal disclaimer.

(21) Appl. No.: 12/043,979

(22) Filed: Mar. 7, 2008

(65) Prior Publication Data

US 2008/0215024 A1    Sep. 4, 2008

Related U.S. Application Data

(63) Continuation of application No. 10/078,816, filed on Feb. 19, 2002, now Pat. No. 7,365,238.

(51) Int. Cl.
*A61F 13/15* (2006.01)
(52) U.S. Cl. .................. 604/361; 600/352; 436/169
(58) Field of Classification Search .......... 604/360–362; 600/352; 436/169
See application file for complete search history.

(56) References Cited

U.S. PATENT DOCUMENTS

| | | | |
|---|---|---|---|
| 3,848,594 A | 11/1974 | Buell | |
| 3,860,003 A | 1/1975 | Buell | |
| 3,911,173 A | 10/1975 | Sprague, Jr. | |
| 3,929,135 A | 12/1975 | Thompson | |
| 4,121,011 A | 10/1978 | Glover et al. | |
| 4,231,370 A | 11/1980 | Mroz et al. | |
| 4,318,709 A | 3/1982 | Falb et al. | |
| 4,324,246 A | 4/1982 | Mullane et al. | |
| 4,334,920 A | 6/1982 | Mori et al. | |
| 4,342,314 A | 8/1982 | Radel et al. | |
| 4,351,183 A | 9/1982 | Ehbert | |
| 4,381,781 A | 5/1983 | Sciaraffa et al. | |
| 4,463,045 A | 7/1984 | Ahr et al. | |
| 4,515,595 A | 5/1985 | Kievit et al. | |
| 4,573,986 A | 3/1986 | Minetola et al. | |

(Continued)

FOREIGN PATENT DOCUMENTS

DE    198 37 678 A1    3/2000

(Continued)

OTHER PUBLICATIONS

Chadha, et al., "Measurement of Urinary Concentration: A Critical Appraisal of Methodologies", Pediatric Nephrology, vol. 16, 2001, pp. 374-382, XP-002244663.

(Continued)

*Primary Examiner* — Lynne Anderson
(74) *Attorney, Agent, or Firm* — William E. Gallagher; Thibault Fayette

(57) ABSTRACT

A wearable article comprising a dehydration indicator adapted to measure a urine ionic strength correlated to a specific gravity of the wearer's urine and provide a visible signal when the urine ionic strength reaches a value corresponding to a predetermined threshold of the specific gravity. The wearable article may be a disposable absorbent article. The dehydration indicator may also be comprised in an insert for use with a wearable article. The dehydration indicator may provide qualitative or quantitative information about the ionic strength of the wearer's urine.

9 Claims, 6 Drawing Sheets

U.S. PATENT DOCUMENTS

| | | | |
|---|---|---|---|
| 4,609,518 A | 9/1986 | Curro et al. |
| 4,610,678 A | 9/1986 | Weisman et al. |
| 4,629,643 A | 12/1986 | Curro et al. |
| 4,636,207 A | 1/1987 | Buell |
| 4,662,875 A | 5/1987 | Hirotsu et al. |
| 4,673,402 A | 6/1987 | Weisman et al. |
| 4,695,278 A | 9/1987 | Lawson |
| 4,699,622 A | 10/1987 | Toussant et al. |
| 4,704,115 A | 11/1987 | Buell |
| 4,705,513 A | 11/1987 | Sheldon et al. |
| 4,710,189 A | 12/1987 | Lash |
| 4,785,996 A | 11/1988 | Ziecker et al. |
| 4,795,454 A | 1/1989 | Dragoo |
| 4,808,178 A | 2/1989 | Aziz et al. |
| 4,816,025 A | 3/1989 | Foreman |
| 4,826,550 A | 5/1989 | Shimizu et al. |
| 4,834,735 A | 5/1989 | Alemany et al. |
| 4,842,666 A | 6/1989 | Werenicz |
| 4,846,815 A | 7/1989 | Scripps |
| 4,857,067 A | 8/1989 | Wood et al. |
| 4,888,231 A | 12/1989 | Angstadt |
| 4,892,536 A | 1/1990 | Desmarais et al. |
| 4,894,060 A | 1/1990 | Nestegard |
| 4,900,317 A | 2/1990 | Buell |
| 4,909,803 A | 3/1990 | Aziz et al. |
| 4,931,051 A | 6/1990 | Castello |
| 4,938,753 A | 7/1990 | Van Gompel et al. |
| 4,940,464 A | 7/1990 | Van Gompel et al. |
| 4,946,527 A | 8/1990 | Battrell |
| 4,963,140 A | 10/1990 | Robertson et al. |
| 4,968,312 A | 11/1990 | Khan |
| 4,988,344 A | 1/1991 | Reising et al. |
| 4,988,345 A | 1/1991 | Reising |
| 4,990,147 A | 2/1991 | Freeland |
| 5,006,394 A | 4/1991 | Baird |
| 5,026,364 A | 6/1991 | Robertson |
| 5,037,416 A | 8/1991 | Allen et al. |
| 5,062,840 A | 11/1991 | Holt et al. |
| 5,085,654 A | 2/1992 | Buell |
| 5,092,816 A | 3/1992 | Levasseur |
| 5,137,537 A | 8/1992 | Herron et al. |
| 5,140,393 A | 8/1992 | Hijikihigawa et al. |
| 5,147,345 A | 9/1992 | Young et al. |
| 5,151,092 A | 9/1992 | Buell et al. |
| 5,171,236 A | 12/1992 | Dreier et al. |
| 5,181,905 A * | 1/1993 | Flam ........................ 602/41 |
| 5,197,958 A | 3/1993 | Howell |
| 5,221,228 A | 6/1993 | Pedroia |
| 5,221,274 A | 6/1993 | Buell et al. |
| 5,242,436 A | 9/1993 | Weil et al. |
| 5,246,433 A | 9/1993 | Hasse et al. |
| 5,260,345 A | 11/1993 | Desmarais et al. |
| 5,269,755 A | 12/1993 | Bodicky |
| 5,269,775 A | 12/1993 | Freeland et al. |
| 5,306,266 A | 4/1994 | Freeland |
| 5,342,338 A | 8/1994 | Roe |
| 5,387,207 A | 2/1995 | Dyer et al. |
| 5,389,093 A | 2/1995 | Howell |
| 5,397,318 A | 3/1995 | Dreier |
| 5,458,140 A | 10/1995 | Eppstein et al. |
| 5,468,236 A * | 11/1995 | Everhart et al. ........... 604/361 |
| 5,492,751 A | 2/1996 | Butt, Sr. et al. |
| 5,499,978 A | 3/1996 | Buell et al. |
| 5,507,736 A | 4/1996 | Clear et al. |
| 5,507,760 A | 4/1996 | Wynne et al. |
| 5,514,121 A | 5/1996 | Roe et al. |
| 5,518,801 A | 5/1996 | Chappell et al. |
| 5,540,671 A | 7/1996 | Dreier |
| 5,554,142 A | 9/1996 | Dreier et al. |
| 5,554,143 A | 9/1996 | Roe et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| H1630 H | 1/1997 | Roe et al. |
| 5,591,152 A | 1/1997 | Buell et al. |
| 5,609,587 A | 3/1997 | Roe |
| 5,625,222 A | 4/1997 | Yoneda et al. |
| 5,635,191 A | 6/1997 | Roe et al. |
| H1670 H | 7/1997 | Aziz et al. |
| 5,643,588 A | 7/1997 | Roe et al. |
| 5,653,703 A | 8/1997 | Roe et al. |
| 5,669,897 A | 9/1997 | Lavon et al. |
| 5,865,823 A | 2/1999 | Curro |
| 5,897,545 A | 4/1999 | Kline et al. |
| 5,922,283 A | 7/1999 | Hsu |
| 5,938,648 A | 8/1999 | Lavon et al. |
| 5,941,864 A | 8/1999 | Roe |
| 5,947,943 A * | 9/1999 | Lee ............................ 604/361 |
| 5,957,908 A | 9/1999 | Kline et al. |
| 5,968,025 A | 10/1999 | Roe et al. |
| 5,977,430 A | 11/1999 | Roe et al. |
| 5,997,520 A | 12/1999 | Ahr et al. |
| 6,004,306 A | 12/1999 | Robles et al. |
| 6,013,063 A | 1/2000 | Roe et al. |
| 6,106,461 A * | 8/2000 | Roskin et al. ................. 600/309 |
| 6,118,041 A | 9/2000 | Roe et al. |
| 6,120,487 A | 9/2000 | Ashton |
| 6,120,489 A | 9/2000 | Johnson et al. |
| 6,149,636 A | 11/2000 | Roe et al. |
| 6,168,584 B1 | 1/2001 | Allen et al. |
| 6,186,991 B1 | 2/2001 | Roe et al. |
| 6,203,496 B1 * | 3/2001 | Gael et al. ..................... 600/362 |
| 6,399,853 B1 | 6/2002 | Roe et al. |
| 6,432,098 B1 | 8/2002 | Kline et al. |
| 6,476,288 B1 | 11/2002 | Vanrijswijck et al. |
| 6,479,727 B1 * | 11/2002 | Roe ............................ 604/361 |
| 6,515,194 B2 * | 2/2003 | Neading et al. ............. 604/361 |
| 6,617,488 B1 | 9/2003 | Springer et al. |
| 6,627,394 B2 * | 9/2003 | Kritzman et al. .................. 435/4 |
| 6,627,787 B1 | 9/2003 | Roe et al. |
| 6,680,422 B2 | 1/2004 | Roe |
| 6,716,441 B1 | 4/2004 | Osborne et al. |
| 7,002,054 B2 | 2/2006 | Allen et al. |
| 7,105,715 B2 | 9/2006 | Carlucci et al. |
| 7,365,238 B2 * | 4/2008 | Diehl et al. ................... 604/361 |
| 2003/0233082 A1 | 12/2003 | Kline et al. |
| 2004/0087922 A1 | 5/2004 | Bobadilla |
| 2005/0177120 A1 | 8/2005 | Olson et al. |
| 2006/0025732 A1 | 2/2006 | Ying et al. |
| 2007/0270773 A1 | 11/2007 | Mackey |
| 2008/0021423 A1 | 1/2008 | Klofta et al. |
| 2008/0021428 A1 | 1/2008 | Klofta et al. |
| 2008/0021429 A1 | 1/2008 | Klofta et al. |

FOREIGN PATENT DOCUMENTS

| | | |
|---|---|---|
| DE | 203 13 784 U1 | 12/2003 |
| EP | 0 114 315 B1 | 6/1987 |
| EP | 0 560 099 A2 | 9/1993 |
| EP | 0 611 966 A1 | 8/1994 |
| JP | 60-161108 | 8/1985 |
| JP | 01-266202 | 10/1989 |
| JP | 05-180846 | 7/1993 |
| JP | 06-063027 | 9/1994 |
| JP | 10-313894 A | 12/1998 |
| JP | 2001-327530 A | 11/2001 |
| JP | 2009-018183 A | 1/2009 |
| WO | WO-94/14395 A1 | 7/1994 |
| WO | WO-94/24557 A1 | 10/1994 |
| WO | WO-95/16746 A1 | 6/1995 |
| WO | WO-95/24173 A2 | 9/1995 |
| WO | WO-97/34014 A1 | 9/1997 |
| WO | WO-98/27417 A1 | 6/1998 |
| WO | WO-99/31486 A1 | 6/1999 |
| WO | WO-01/54552 C2 | 1/2001 |
| WO | WO-01/50996 A1 | 7/2001 |
| WO | WO-01/54552 A1 | 8/2001 |
| WO | WO-03/002050 A2 | 1/2003 |
| WO | WO-2007/077538 A1 | 7/2007 |

OTHER PUBLICATIONS

A Reagent Strip for Measuring the Specific Gravity of Urine, *Clinical Chemistry*, 28/10, 2068-2072 (1982).

* cited by examiner

ABSORBENT ARTICLE HAVING A DEHYDRATION INDICATOR

CROSS REFERENCE TO RELATED APPLICATION

This application is a continuation of application Ser. No. 10/078,816, filed Feb. 19, 2002, now U.S. Pat. No. 7,365,238, the substance of which is incorporated herein by reference

FIELD OF THE INVENTION

This invention is directed to a dehydration indicator that may be used in conjunction with a wearable article. More particularly, the invention relates to hygienic absorbent articles, such as diapers, adult incontinence articles, feminine protection articles and the like including a dehydration indicator.

BACKGROUND OF THE INVENTION

Wearable and absorbent articles are well known in the art. Absorbent articles typically have an absorbent core, which is held or positioned against the body of the wearer during use by a fastening system, such that the bodily exudates are caught by the article. Typical absorbent articles include a topsheet facing the wearer which permits fluid exudates to pass through and a backsheet which prevents the exudates from escaping from the absorbent article. Many advancements have been made in the art since the introduction of the disposable absorbent article. However, most of these articles are not adapted to aid the caregiver in the monitoring of the health of the wearer. Certain attempts have been made in the art to include analysis of components of human waste, such as urine and feces, to provide indication of various specific health issues such as infections (e.g., urinary tract infections, etc.). For example, U.S. Pat. No. 5,468,236 issued to Everhart et al. on Nov. 21, 1995 discloses a disposable absorbent product that includes a chemically reactive means having an end point adapted to provide a visual indicator of the presence of a substance in mammalian bodily excrement. However, the prior art fails to provide the caregiver with a means of monitoring for the early indication of the onset of dehydration, often resulting in a delay in recognition of, and the ultimate diagnosis and treatment of, this issue for the wearer. Thus, it would be desirable to provide wearable articles with the capability to detect signals related to a dehydrated state of a wearer.

SUMMARY OF THE INVENTION

The present invention is directed to a wearable article comprising a dehydration indicator. The dehydration indicator is adapted to measure a urine ionic strength correlated to a specific gravity of the wearer's urine. The dehydration indicator provides a visible signal when the urine ionic strength reaches a value corresponding to a predetermined threshold value of the specific gravity. The threshold value is set at a level commonly accepted as being indicative of slight, moderate, or severe dehydration.

DETAILED DESCRIPTION OF THE INVENTION

The present invention is directed to a dehydration indicator that may be used in conjunction with a wearable article, including but not limited to disposable absorbent articles. As used herein, the term "wearable article" refers to articles adapted to be applied or affixed to, or otherwise associated with a portion of a wearer's anatomy for a certain period of time, and often during a wearer's normal activities. Wearable articles may encircle or at least partially enclose a portion of a wearer's body, such as in the case of belts, diapers, training pants, underwear, other garments, and the like. Such wearable articles may include elastically extensible and/or fastening components to ensure a proper fit to the wearer and/or fastening components to provide for convenient application and removal of the article from the wearer by a caregiver. Alternatively, in addition to the above described features, at least a portion of the wearable article may be adhesively affixed to the skin of the wearer. In some embodiments, the wearable article may include a separate element, such as an insert, affixed to or associated with the wearable article. Although not limited to such embodiments, the present invention will generally be described below as associated with a disposable absorbent article.

As used herein, the term "absorbent article" refers to devices that absorb and contain body exudates and, more specifically, refers to devices that are placed against or in proximity to the body of the wearer to absorb and contain the various exudates discharged from the body. The term "disposable" is used herein to describe absorbent articles that generally are not intended to be laundered or otherwise restored or reused as absorbent articles, i.e., they are intended to be discarded after a single use and, preferably, to be recycled, composted or otherwise discarded in an environmentally compatible manner. A "unitary" absorbent article refers to absorbent articles that are formed of separate parts united together to form a coordinated entity so that they do not require separate manipulative parts like a separate holder and/or liner. A preferred absorbent article embodiment of the present invention is the unitary disposable absorbent article, diaper 20, shown in FIG. 1. As used herein, the term "diaper" refers to an absorbent article generally worn by infants and incontinent persons about the lower torso. The present invention is also applicable to other wearable and absorbent articles such as incontinence briefs, incontinence undergarments, absorbent inserts, diaper holders and liners, feminine hygiene garments, bandages and the like.

Figure 1:
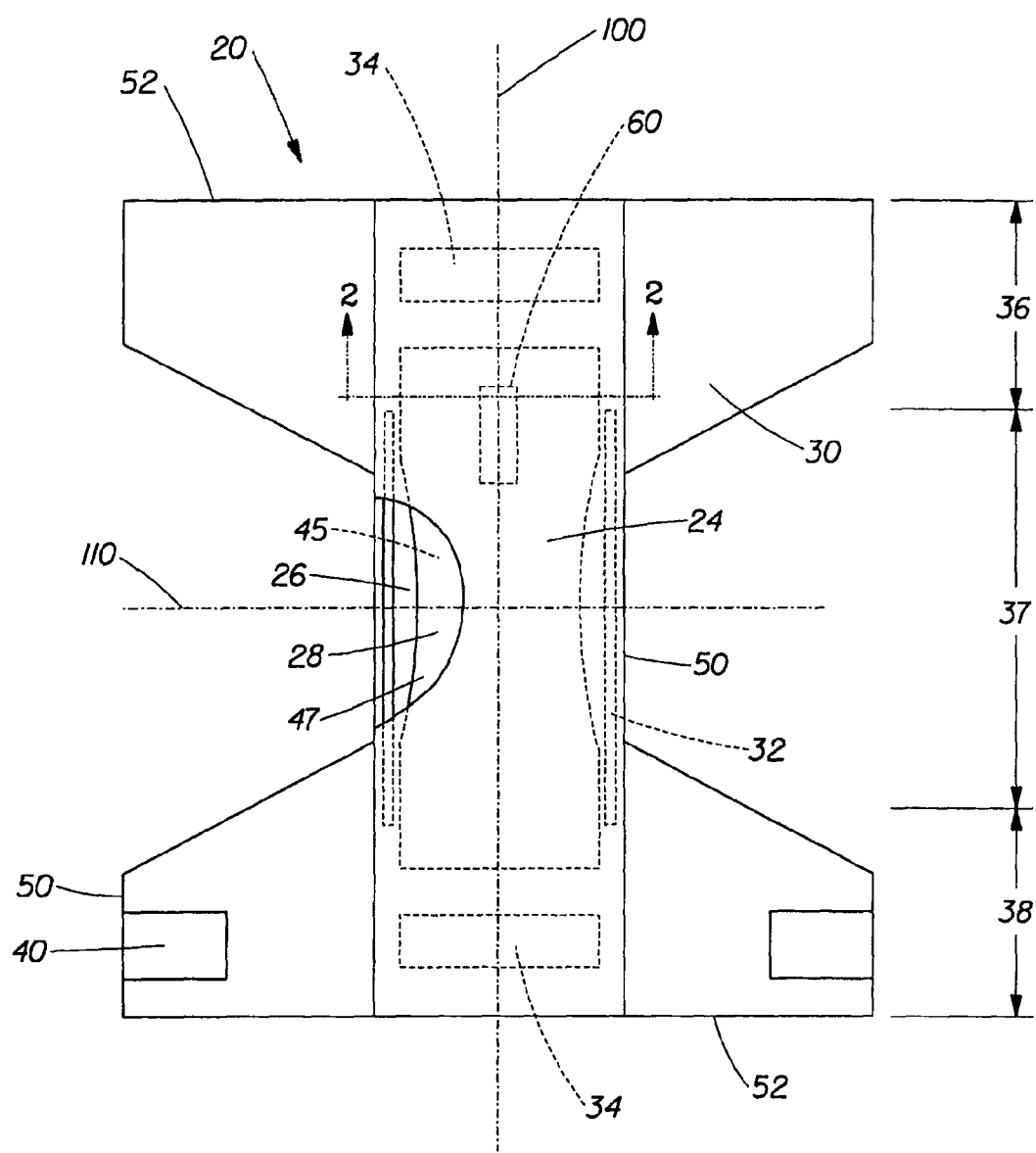
FIG. 1 is a plan view of a disposable diaper embodiment of the present invention.

FIG. 1 is a plan view of the diaper 20 of the present invention in a flat-out state with portions of the structure being cut-away to more clearly show the construction of the diaper 20. The portion of the diaper 20 that faces the wearer is oriented towards the viewer. As shown in FIG. 1, the diaper 20 preferably comprises a liquid pervious topsheet 24; a liquid impervious backsheet 26; an absorbent core 28 that is preferably positioned between at least a portion of the topsheet 24 and the backsheet 26; side panels 30; elasticized leg cuffs 32; an elastic waist feature 34; and a fastening system generally designated 40. The diaper 20 is shown in FIG. 1 to have a first waist region 36, a second waist region 38 opposed to the first waist region 36 and a crotch region 37 located between the first waist region 36 and the second waist region 38. The periphery of the diaper 20 is defined by the outer edges of the diaper 20 in which longitudinal edges 50 run generally parallel to the longitudinal centerline 100 of the diaper 20 and end edges 52 run between the longitudinal edges 50 generally parallel to the lateral centerline 110 of the diaper 20.

While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; U.S. Pat. No. 5,580,411 entitled "Zero Scrap Method For Manufacturing Side Panels For Absorbent Articles" issued to Nease et al. on Dec. 3, 1996; and U.S. Pat. No. 6,004,306 entitled "Absorbent Article With Multi-Directional Extensible Side Panels" issued to Robles et al. 15 on Dec. 21, 1999; each of which is hereby incorporated herein by reference.

The backsheet 26 is generally that portion of the diaper 20 positioned adjacent garment facing surface 45 of the absorbent core 28 that prevents the exudates absorbed and contained therein from soiling articles that may contact the diaper 20, such as bedsheets and undergarments. The topsheet 24 is preferably positioned adjacent body facing surface 47 of the absorbent core 28 and may be joined thereto and/or to the backsheet 26 by any attachment means known in the art. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element. The topsheet 24 is preferably compliant, soft-feeling, and non-irritating to the wearer's skin. Further, at least a portion of the topsheet 24 is liquid pervious, permitting liquids to readily penetrate through its thickness.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

As noted above, the diaper 20 may also include a fastening system 40. The fastening system 40 preferably maintains the first waist region 36 and the second waist region 38 in a configuration so as to provide lateral tensions about the circumference of the diaper 20 to hold the diaper 20 on the wearer. The fastening system 40 preferably comprises a surface fastener such as tape tabs, hook and loop fastening components and/or hermaphroditic fastening components, although any other known fastening means are generally acceptable. In alternative embodiments, opposing sides of the article may be seamed or welded to form a pant. This allows the article to be used as a pull-on type diaper, such as a training pant.

The article of the present invention further comprises a dehydration indicator 60 that provides a qualitative or quantitative indication to a caregiver of the presence or degree of dehydration of the wearer of the article. It is typical in medical practice to use either urine osmolality or urine specific gravity to indicate the presence or degree of dehydration in human subjects. As is known in the art, osmolality is the concentration of an osmotic solution especially when measured in osmols or milliosmols per 1000 grams of solvent, with an osmol being a standard unit of osmotic pressure based on a one molal concentration of an ion in a solution. As the level of water in the subject's body, i.e., the level of hydration, decreases, the urine becomes more concentrated and its osmolality and specific gravity increase above commonly accepted thresholds. It is commonly accepted that urine osmolality is the most accurate measure of urine concentration as it is the measure most closely related to the physiology of urine concentration, in which the kidneys concentrate the urine based on the osmolal gradient. The specific gravity (SG) of the urine is also considered a valid estimate of urine concentration and can be converted into approximate osmolality by Equation 1.

$$\mathrm{mOsm/kg\ H_2O} = (SG - 1.000) \times 40{,}000 \qquad \text{Equation 1}$$

Comprehensive descriptions of the various methods of measuring and/or estimating urine concentration are presented in the following publications, the disclosures of which are hereby incorporated herein by reference: Chadha, et al, "Measurement of Urinary Concentration: a Critical Appraisal of Methodologies", *Pediatric Nephrology* (2001), 16:374-382; and Burkhardt, et al, "A Reagent Strip for Measuring the Specific Gravity of Urine", *Clinical Chemistry,* 28/10, 2068-2072 (1981).

The osmolality of urine is often measured in medical laboratories using either a freezing point osmometer (i.e., to measure freezing point depression) or a vapor pressure osmometer (i.e., to measure vapor pressure depression). Medical laboratories typically use a refractometer or hydrometer to measure the specific gravity of urine. However, these laboratory-based approaches to measuring urine osmolality or specific gravity are time consuming and require specialized equipment and/or training. Since the specific gravity of urine is correlated to the ionic strength of the urine, measurements of urine ionic strength are commonly used to estimate specific gravity in rapid screening assessments for the presence or severity of dehydration in a human subject. Accordingly, the dehydration indicator of the present invention is preferably responsive to elevated urine ionic strength and preferably provides an estimate of the urine specific gravity.

In certain embodiments, the dehydration indicator 60 may provide a qualitative visual indication that the ionic strength of the wearer's urine, and therefore the specific gravity of the urine, is above one or more predefined threshold values. The threshold values are preferably set at one or more levels commonly accepted as being indicative of slight, moderate, and/or severe dehydration. For example, in the United States, a 3-5% fluid deficit is commonly termed "mild" dehydration, commonly presenting symptoms of increased thirst, slightly dry mucous membranes, and dry warm skin. A 6-9% fluid deficit is typically regarded as "moderate" dehydration and may be accompanied by loss of skin turgor, dry mucous membranes, lack of tears, and poor blood profusion to the extremities. Fluid deficits of 10% or greater are termed "severe" dehydration and may present, in addition to the above symptoms, a sunken fontanel, lethargy, altered consciousness, and rapid deep breathing. Treatment of mild dehydration typically involves careful oral fluid replacement at home, while for moderate and severe dehydration medical attention should be sought, typically requiring intravenous fluid replacement.

Therefore, the dehydration indicator 60 may be designed, for example, to indicate to a mother or other caregiver when the specific gravity of the urine is in the range of about 1.020 to about 1.024, indicating mild dehydration, in the range of about 1.025 to about 1.029, indicating moderate dehydration, or above 1.030, indicating severe dehydration and the risk of anuria. In such cases, the dehydration indicator 60 functions as an "early warning" of dehydration and a signal to contact a physician and/or begin remedial treatment, such as administering electrolyte solutions orally, i.e., to initiate fluid replacement therapy. Table 1 provides data relating urine osmolality and average specific gravity for newborn infants from the Chadha, et al, reference above.

TABLE 1

| Urine Osmolality (mOsml/kg) | Urine Specific Gravity (via refractometer) |
|---|---|
| 100 | 1.0055 |
| 200 | 1.011 |
| 300 | 1.016 |
| 400 | 1.0215 |
| 500 | 1.027 |
| 600 | 1.033 |

Table 2 provides data relating solution ionic strength to specific gravity measured via a refractometer, specific gravity measured using CHEMSTRIP™ urinalysis strips, and the qualitative color of the CHEMSTRIP™ urinalysis strips for various dilutions of a synthetic urine. Note: the urea content was not included in the calculation of synthetic urine ionic strength.

TABLE 2

| Synthetic Urine Component | Grams dissolved in 2000 ml deionized $H_2O$ | Grams dissolved in 300 ml deionized $H_2O$ | Grams dissolved in 185 ml deionized $H_2O$ | Grams dissolved in 110 ml deionized $H_2O$ | Grams dissolved in 80 ml deionized $H_2O$ | Grams dissolved in 55 ml deionized $H_2O$ |
|---|---|---|---|---|---|---|
| Urea | 3.20 | 3.20 | 3.20 | 3.20 | 3.20 | 3.20 |
| $(NH_4)H_2PO_4$ | 0.153 | 0.153 | 0.153 | 0.153 | 0.153 | 0.153 |
| $(NR_4)_2HPO_4$ | 0.027 | 0.027 | 0.027 | 0.027 | 0.027 | 0.027 |
| $CaCl_2 \cdot 2H_2O$ | 0.184 | 0.184 | 0.184 | 0.184 | 0.184 | 0.184 |
| $MgCl_2 \cdot 6H_2O$ | 0.130 | 0.130 | 0.130 | 0.130 | 0.130 | 0.130 |
| $Na_2SO_4$ | 0.122 | 0.122 | 0.122 | 0.122 | 0.122 | 0.122 |
| KCl | 1.76 | 1.76 | 1.76 | 1.76 | 1.76 | 1.76 |
| Synthetic Urine Ionic Strength | 0.0169 | 0.113 | 0.183 | 0.307 | 0.422 | 0.615 |
| Specific Gravity via refractometer | 1.002 | 1.008 | 1.014 | 1.020 | 1.025 | 1.035 |
| Specific Gravity via CHEMSTRIP™ at 1 min. | 1.005 | 1.010 | 1.015 | 1.020 | 1.025 | Off Scale >1.030 |
| Color of CHEMSTRIP™ SG segment | Dark Blue/Green | Green/Blue | Olive Green | Tan/Brown | Light Tan | Orange |

Figure 2A:
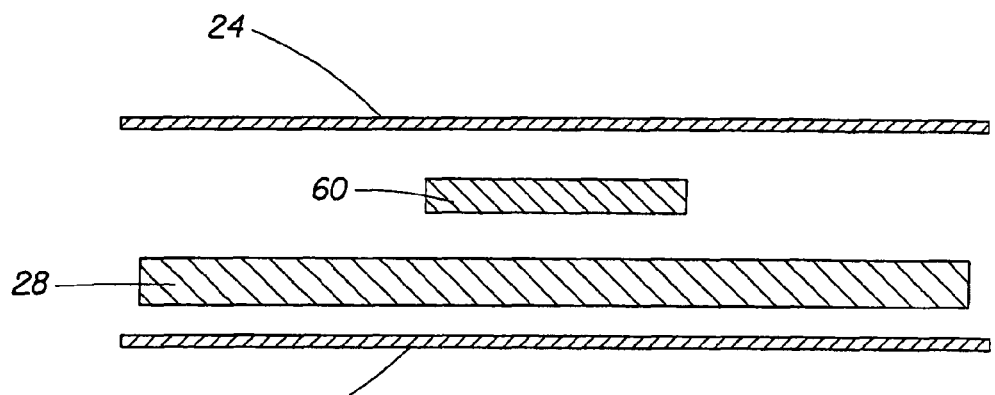
FIGS. 2A and 2B show a section view of a portion of alternative disposable diaper embodiments of FIG. 1.
Figure 2B:
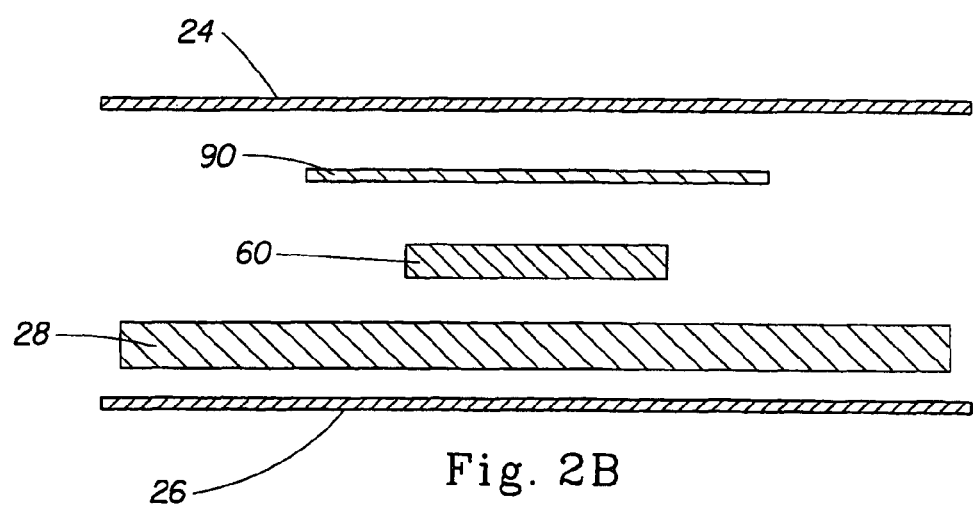

In certain alternate embodiments, the dehydration indicator 60 may provide a more continuous indication of the status of the wearer's hydration level. For example, the dehydration indicator may change color, e.g., from blue to tan, or intensity as the ionic strength, and therefore the specific gravity, of the urine increases. The caregiver may then infer the degree of dehydration by comparing the color of the dehydration indicator to a diagnostic color chart. Alternatively, as shown in FIG. 2B, a translucent cover 90 having the same or similar shade as the dehydration indicator when it indicates a "normal" urine ionic strength/specific gravity may mask the dehydration indicator 60. In this embodiment, as the ionic strength/specific gravity of the urine increases and the dehydration indicator color changes, the dehydration indicator signal becomes visible due to its contrast/color difference versus the translucent mask 90. For example, in the embodiment described above, the dehydration indicator 60 may comprise a translucent masking cover 90 having a blue color as a top layer. As the urine ionic strength increases and the color shifts to tan, the signal will become visible through the cover 90 due to the contrast differences between the signal and the translucent cover 90.

Figure 3:
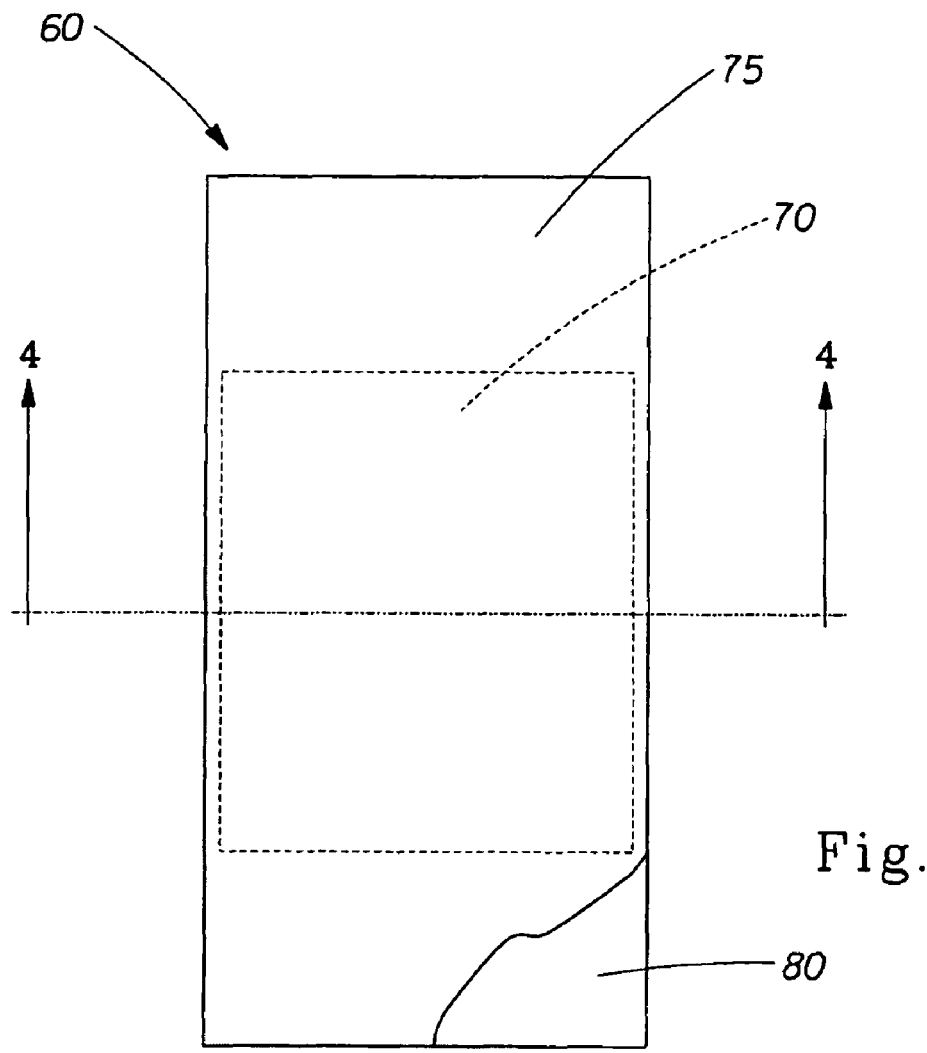
FIG. 3 shows a generic qualitative dehydration indicator.
Figure 6:
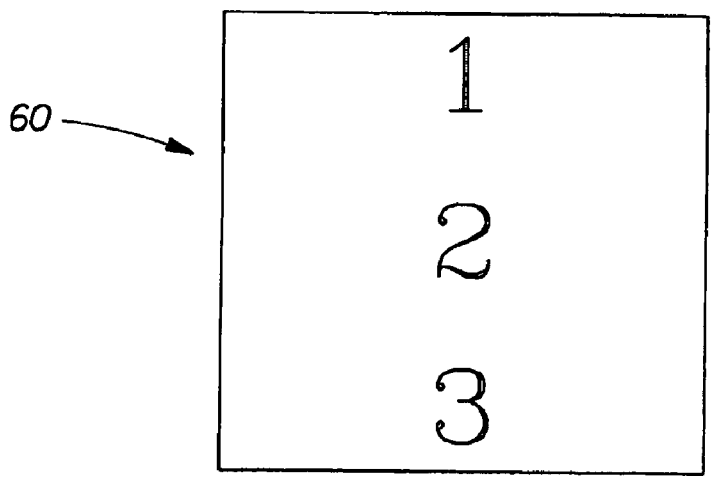
FIG. 6 shows an alternative dehydration indicator having numeric designations.

Elevated urine ionic strength correlated to a urine specific gravity indicative of some level of dehydration may be signaled to the caregiver via visual, audible, and/or tactile signals. In preferred embodiments of the present invention, a visual signal is provided to the caregiver by the dehydration indicator 60. Examples of visual signals include having a color or pattern appear, disappear, or change in color, shape, or design, or any combination thereof. The pattern may, for example, include one or more stripes, dots, alphanumeric characters, symbols, or pictures, or any combination thereof. FIG. 3 depicts a qualitative dehydration indicator wherein the smaller box 65 changes color when contacted by urine having an ionic strength corresponding to a specific gravity above a threshold value. FIG. 6 depicts a qualitative dehydration indicator wherein the alphanumeric designations "1", "2", or "3" appear when contacted by urine having an ionic strength/specific gravity indicative of "mild, "moderate", or "severe"

dehydration, respectively, as currently understood in the medical field and as described above.

Figure 5:
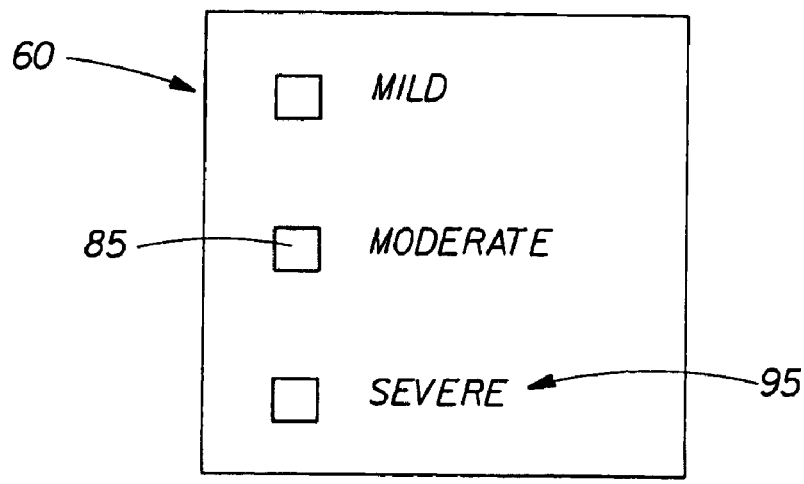
FIG. 5 shows a qualitative dehydration indicator having alphanumeric designations of the level of dehydration.
Figure 7:
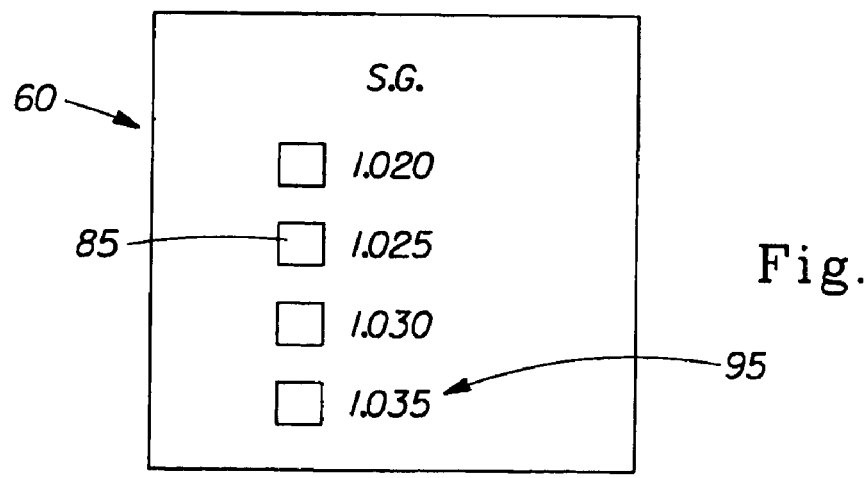
FIG. 7 shows a dehydration indicator having numerical values beside colored dots.
Figure 8:
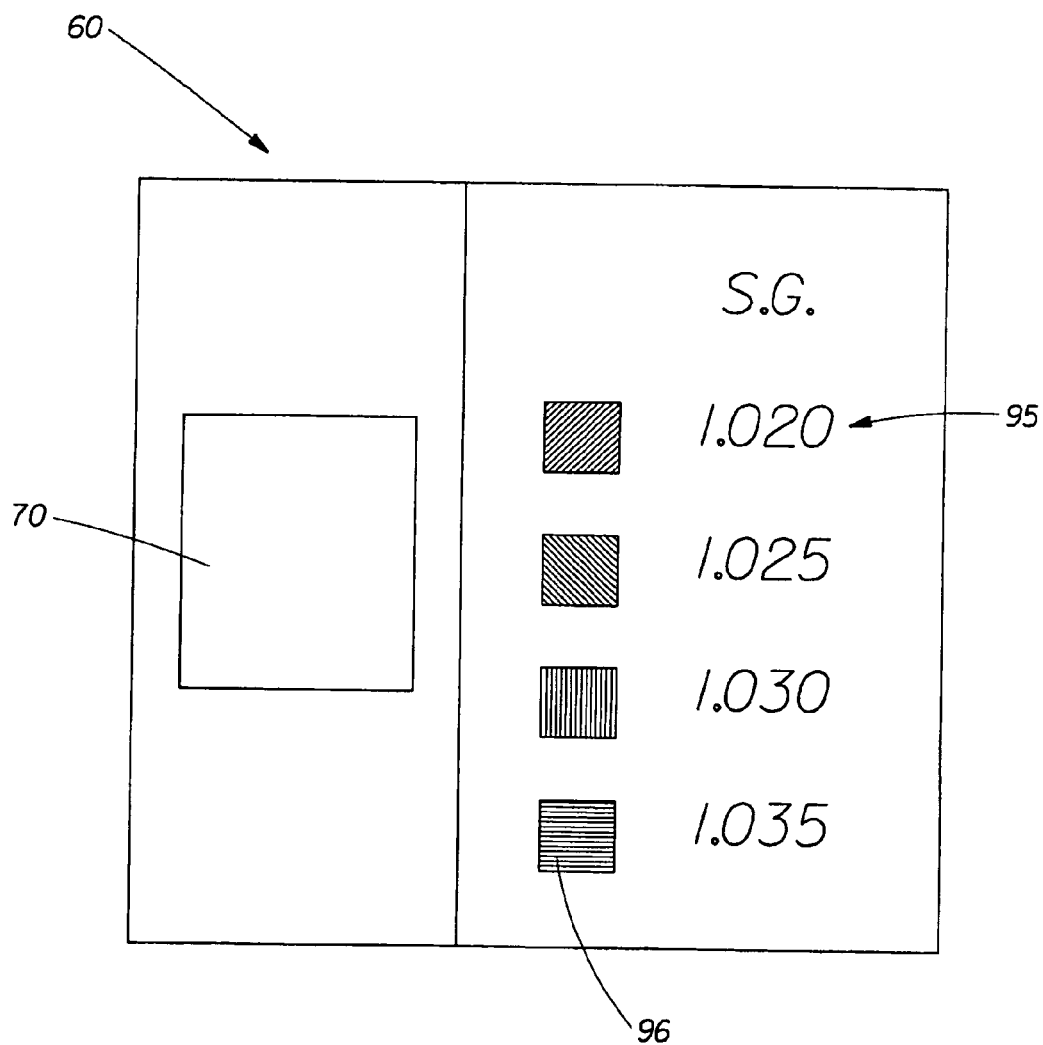
FIG. 8 shows a dehydration indicator having a color key beside a single colored dot.

The dehydration indicator 60 may have the capability to indicate multiple urine ionic strength/specific gravity thresholds, providing a more quantitative indication of the presence or degree of dehydration. For example, the dehydration indicator 60 may indicate three urine ionic strength and/or specific gravity thresholds, indicating slight, moderate and severe dehydration. In a nonlimiting example, as shown in FIG. 5, the dehydration indicator 60 may provide separate signals for urine ionic strengths at levels associated with mild, moderate, and/or severe dehydration. Alternatively, the dehydration indicator 60 may include a multiplicity of urine ionic strength/specific gravity thresholds, each providing a separate signal, at regular intervals through the urine concentration region of interest. For example as shown in FIG. 7, the dehydration indicator 60 may have urine specific gravity thresholds (as estimated by urine ionic strength) at intervals of 0.005. In embodiments having more than one urine ionic strength/specific gravity threshold, the dehydration indicator 60 may provide different visual signals for each threshold (i.e., a different color, symbol, alphanumeric symbol, shape, etc., or combination thereof). In certain embodiments, two or more different urine ionic strength indicating chemistries having different dry and/or wet state colors may be employed to improve the interpretation of the signal from the dehydration indicator 60. For example, one urine ionic strength indicating chemistry may have a blue color when dry and a tan color when wet and a second urine ionic strength indicating chemistry may have a blue color when dry, but a red color when wet. In this example, the relative color change between the two indicators when wetted by urine having an ionic strength above a pre-defined threshold value is accentuated. In certain embodiments, each threshold may comprise a simple signal, e.g., a colored shape 85, next to an indicium 95 on the carrier element, examples of which are shown in FIGS. 5 and 7. Alternatively, as shown in FIG. 8, the indicia may comprise one or more colored zones 96 with which to compare the color of the dehydration indicating composition 70 following contact of urine with the dehydration indicator in order to assess the presence and/or severity of a dehydrated condition, i.e., the indicia may comprise a color key for the dehydration indicator signal.

Regardless of the number of urine ionic strength/specific gravity thresholds and/or the nature of the signal, the dehydration indicator 60 preferably provides a signal sufficiently durable, i.e., long lasting, so as to be readable at any time between the triggering urination event and the removal of the article by a caregiver. Typically, the signal should be visible for at least about 1 hour after contact with urine. Preferably, the signal should be visible for at least about 2 hours, and more preferably at least about 12 hours, after contact with urine.

Upon contact with urine having an ionic strength/specific gravity above the predefined threshold value, the dehydration indicator 60 should respond, i.e., provide a visible signal, prior to the time when the urine has dried or been contaminated to ensure the accuracy of the ionic strength measurement. If the response is delayed too long, the accuracy of the measurement of urine ionic strength may be adversely affected by either the artificial concentration of the urine by evaporation of its water component or the addition of ionic solutes in the form of contaminants. Typically, the dehydration indicator 60 provides a signal within about 5 minutes of contacting urine. Preferably, the dehydration indicator 60 provides a signal within about 1 minute, and more preferably within about 20 seconds, of contacting urine.

A qualitative dehydration indicator 60 may indicate an elevated urine ionic strength (i.e., specific gravity) by having a color or pattern appear, disappear, or change in color, shape, or design, or any combination thereof. The pattern may, for example, include one or more stripes, dots, alphanumeric characters, symbols, or pictures, or any combination thereof. The dehydration indicator 60 may be visible from inside the article or outside the article and may be affixed to or disposed with any component of the article. For example, the dehydration indicator 60 may be affixed to the topsheet 24, the absorbent material 28, inner leg cuffs, also known as barrier cuffs (not shown in the drawings), or the backsheet 26. In certain preferred embodiments, a non-limiting example of which is depicted in FIG. 2A, the dehydration indicator 60 is positioned directly beneath the topsheet 24 and is visible after the article is at least partially removed from the wearer. In certain alternative embodiments, the dehydration indicator 60 may be positioned on the inside of the article such that it can be seen through at least a portion of the outer cover. In yet other embodiments, the dehydration indicator 60 may be disposed on the article in such a way that a patch or portion of the article can be pulled away, permanently or temporarily, such that the indicator is visible without the article being removed from the wearer. In yet other embodiments, the dehydration indicator 60 may comprise a separate element applied to the article by the caregiver, such as a diaper insert or other carrier element affixed to the topsheet 24, i.e., via adhesive, a mechanical fastener, friction, etc., by the caregiver prior to applying the article to the wearer.

For a given dehydration indicating composition 70, the specific color change associated with urine having various ionic strengths and specific gravities, e.g., various threshold values, must be determined via application of urine or synthetic urine having known specific gravities (preferably at the threshold values) and careful observation and recording of the resultant color of the dehydration indicating composition 70. Preferably, the interpretation of the signal by the caregiver is facilitated via a translucent mask 90, indicia on the dehydration indicator 60 functioning as a color key 110 as shown in FIG. 8, a separate color key provided by the manufacturer, or any other visual means based on the defined color changes associated with the ionic strength/specific gravity threshold value(s) for the given dehydration indicating composition 70.

The dehydration indicator 60, or any of the components thereof such as a dehydration indicating composition 70, may be applied to a substrate, such as the article or any component thereof, or to a carrier element, via any means known in the art. For dehydration indicators, or components thereof, that are applied in a liquid state to the substrate in a continuous or intermittent mode, or in patterns, suitable exemplary processes include slot coating, gravure printing, inkjet printing, spraying, screening, and the like. The indicator may also be applied to the substrate or article in a solid form, such as films, webs, fibers, or particles via continuous unwind processes, cut & slip processes, air deposition, and the like, and may be joined to the substrate via physical entanglement, entrapment, adhesives or any other means as known in the art. If the dehydration indicating composition 70 is applied to the substrate in an aqueous form, the dehydration indicating composition may be subsequently dried to remove any excess water.

Figure 4:
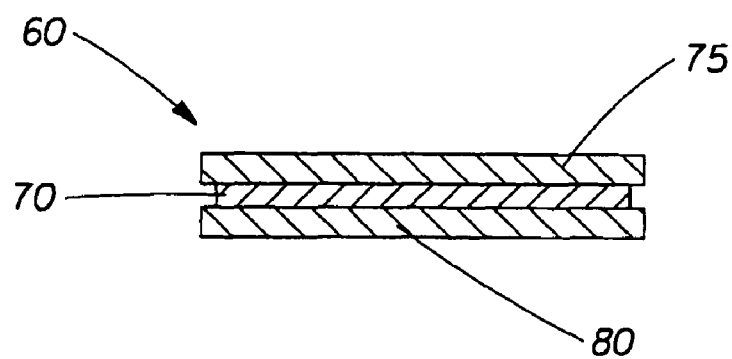
FIG. 4 shows a section view of a portion of the dehydration indicator of FIG. 3.

As noted above and shown in FIGS. 3 and 4, the dehydration indicator 60 may comprise a dehydration indicating composition 70 disposed on or in a substrate, or carrier element 80. The carrier element 80 may comprise a web-like component such as a film, woven or nonwoven material, foam, scrim, or celluosic material, to which the dehydration indicating composition or element is applied or affixed. Alternately, the carrier 80 may enclose or encapsulate a dehydration indicating composition to prevent its migration or loss within the article before or during use. In these embodiments, the carrier 80 may comprise one layer folded back upon itself or may comprise a multiplicity of layers. If more than one layer is employed, the various layers may have different properties or comprise different materials. For example, a dehydration indicating composition 70 may be disposed between a permeable top (i.e., wearer-facing) layer and an impermeable bottom layer. In certain embodiments, the top layer may alternatively comprise a selectively permeable layer 75, a dissolving layer, a pH sensitive layer, or a coating. Exemplary selectively permeable layers may include meshes, tissues, micro or macroporous films, semipermeable membranes, and other selectively permeable materials as known in the art. Suitable exemplary semipermeable membranes include cellulose acetate, cellulose diacetate, cellulose triacetate, agar acetate, beta glucan acetate, polymeric epoxides, semipermeable polyurethanes, and semipermeable polyglycolic acid. In certain alternate embodiments, the dehydration indicator 60 may be detachable from the article.

While the dehydration indicator 60 may be located at any point in the article likely to be contacted by urine, the dehydration indicator 60 is preferably located in the portion of the article coordinated with the urine loading point, i.e., the location in which the urine typically insults the article. For instance, the dehydration indicator 60 may be located on or affixed to the topsheet, backsheet, and/or inner leg cuffs. Preferably, the urine ionic strength is measured at or near the topsheet of the article, e.g., on the wearer facing side or underside of the topsheet, in order to minimize the likelihood of contamination of the urine by other components of the article, such as the absorbent core. In many occurrences where the dehydration indicator is located at or near the inner surface of the backsheet, or on any carrier disposed on the underside of an absorbent core, the dehydration indicator may be limited to detecting an elevated urine ionic strength for only the initial urine loading event since relatively large quantities of existing fluid held in the absorbent core may leach electrolytes from absorbent materials such as cellulosic fibers, absorbent foams, and/or superabsorbent polymers which could result in an erroneous urine ionic strength measurement.

Figure 9:
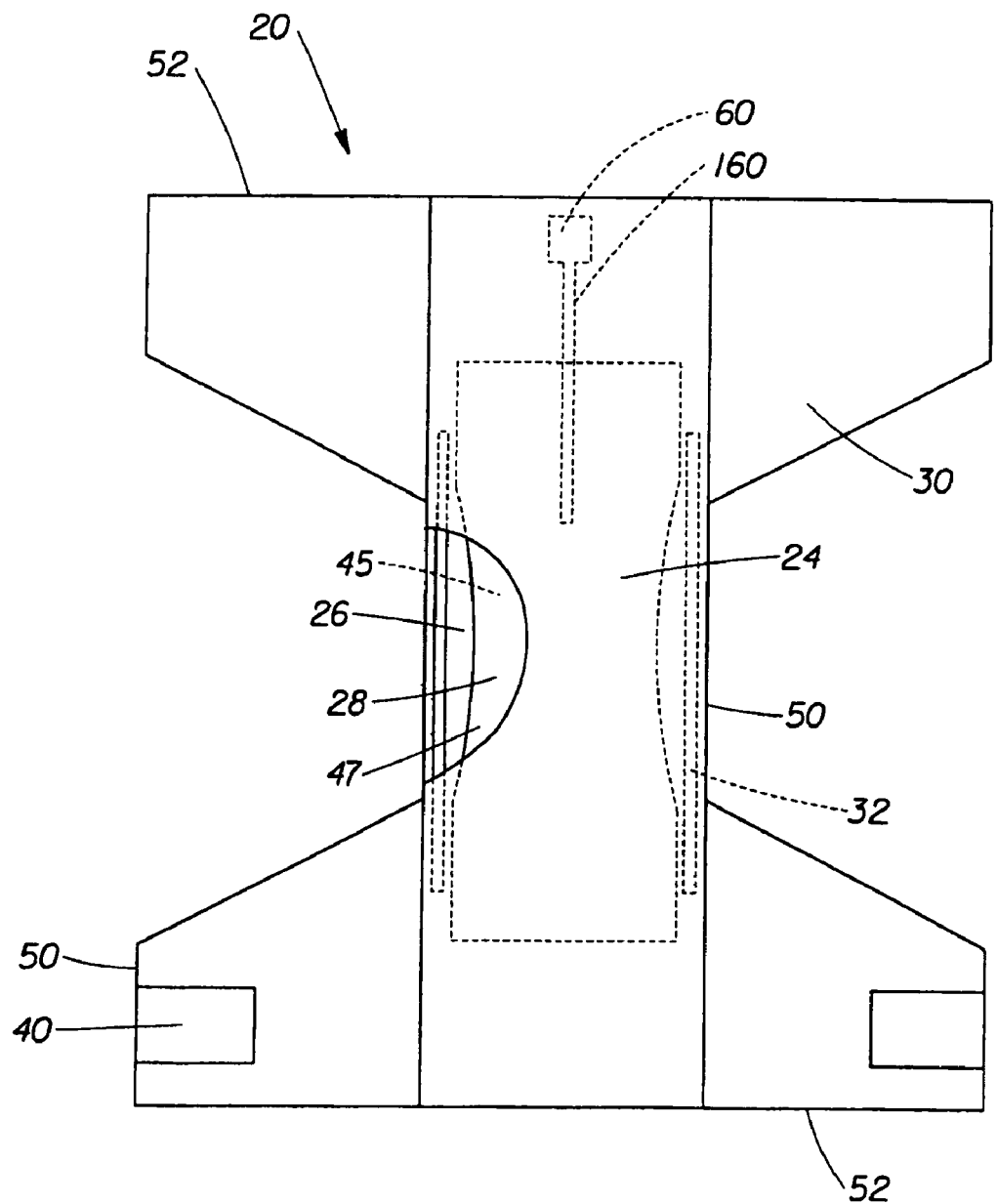
FIG. 9 shows a disposable diaper embodiment having a fluid transport element.

In certain alternate embodiments of the present invention, a nonlimiting example of which is depicted in FIG. 9, the dehydration indicator 60 may be located in regions of the article other than the urine loading zone. In these embodiments, urine is transported to the urine indicator 60 from the urine loading zone by a fluid transport element 100 in fluid communication with the dehydration indicator 60. In these embodiments, at least a portion of the fluid transport element 100 is located in, or adjacent to, the urine loading zone in order to acquire fluid prior to transporting, e.g., wicking, fluid to the dehydration indicator 60. The fluid transport element 100 may comprise any material or structure as known in the art which is capable of transporting fluid from the urine loading zone to the dehydration indicator. Suitable materials for the fluid transport element 100 include cellulosic materials, e.g., fluff, airfelt, wetlaid fibers webs, tissues, foams, nonwovens, sponges, capillary channel fibers, and the like. Alternatively, the fluid transport element may comprise two or more layers of fluid impermeable material having one or more capillary openings between at least two of the layers, the capillary openings providing fluid communication between the urine source and the dehydration indicator.

EXEMPLARY EMBODIMENTS

Example 1

A wearable article having a qualitative dehydration indicator may be constructed as follows:
a) An aqueous urine ionic strength indicating solution is prepared according to the formula:
  1.0 liter of deionized water
  0.120 moles Nitrilo-tris-(methylenephosphonic acid)
  1.5 grams bromothymol blue indicator
b) The pH of the solution from a) above is titrated to a final pH in the range of about pH 7.9 to about 8.1 using a 3.5 N aqueous tetramethylammonium hydroxide solution. The pH is measured using a standard electronic pH meter calibrated according to the manufacturer's instructions. The 3.5 N aqueous tetramethylammonium hydroxide solution is added in volume increments as described below and the pH meter reading is allowed to stabilize after each incremental volume prior to the addition of the next incremental amount. The solution is continuously mixed during the entire titration process. The 3.5 N aqueous tetramethylammonium hydroxide solution is initially added to the solution from a) in increments of 25 ml until the pH of the resultant solution is in the range of about pH 6.0 to about 6.5. Once the pH reaches this range, the 3.5 N aqueous tetramethylammonium hydroxide solution is added in increments of 10 ml until the pH of the resultant solution is in the range of about pH 7.0 to about 7.5. Subsequently, the 3.5 N aqueous tetramethylammonium hydroxide solution is added in incremental volumes of 0.1 to 1.0 ml until the desired pH range of about 7.9 to about 8.1 is attained.
c) A piece of white paper towel, such as BOUNTY™ paper towel, available from The Procter & Gamble Co. of Cincinnati, Ohio, U.S.A. is impregnated with the resultant pH-adjusted solution and dried.
d) A strip of the treated paper towel is cut in a rectangular form having dimensions of 0.5 cm×2 cm and is adhesively affixed along its perimeter to the garment-facing side of a disposable diaper topsheet in the crotch or urine loading region of the product.

Example 2

A wearable article having a qualitative dehydration indicator may be constructed as follows:
a) An aqueous urine ionic strength indicating solution is prepared according to the formula:
  1.0 liter of deionized water
  0.060 moles sodium dihydrogen phosphate
  0.040 moles 2-(N-morpholino)-ethanesulfonic acid (MES)
  7.5 grams bis-(aminoethyl-)glycol ether N,N,N',N'-tetraacetic acid
  1.5 grams bromothymol blue indicator
b) The pH of the solution from a) above is titrated to a final pH in the range of about pH 7.9 to about 8.1 using a 10 N aqueous sodium hydroxide solution. The pH is measured using a standard electronic pH meter calibrated according to the manufacturer's instructions. The 10 N aqueous sodium hydroxide solution is added in volume increments as described below and the pH meter reading is allowed to stabilize after each incremental volume prior to the addition of the next incremental amount. The solution is continuously mixed during the entire titration process. The 10 N aqueous sodium hydroxide solution is initially added to the solution from a) in increments of 5 ml until the pH of the resultant solution is in the range of about pH 6.0 to about 6.5. Once the pH reaches this range, the 10 N aqueous sodium hydroxide solution is added in increments of 1.0 ml until the pH of the resultant solution is in the range of about pH 7.0 to about 7.5. Subsequently, the 10 N aqueous sodium hydroxide solution is added in incremental volumes of 0.1 ml until the desired pH range of about 7.9 to about 8.1 is attained.

c) A piece of white paper towel, such as BOUNTY™ paper towel, available from The Procter & Gamble Co. 25 of Cincinnati, Ohio, U.S.A. is impregnated with the resultant pH-adjusted solution and dried.

d) A strip of the treated paper towel is cut in a rectangular form having dimensions of 0.5 cm×2 cm and is adhesively affixed along its perimeter to the garment-facing side of a disposable diaper topsheet in the crotch or urine loading region of the product.

Example 3

A wearable article having a qualitative dehydration indicator may be constructed as follows:

a) A solution is prepared consisting of 20 grams of maleic anhydride/methylvinylether copolymer in its free acid form in 1.0 liter of deionized water. The free acid form of the maleic anhydride/methylvinylether copolymer is water soluble and has a mass average molecular weight of about 1,500,000. This copolymer is currently commercially available as GANTREZ™ S-97 from International Specialty Products of Wayne, N.J., U.S.A. This copolymer is commonly designated CAS #25 153 40-06. The CAS# refers to the unique numerical designation assigned to a chemical by the Chemical Abstracts Service (CAS) of Columbus, Ohio, USA, which is a division of the American Chemical Society of Washington, D.C., USA.

b) This solution is titrated with a 10 N sodium hydroxide solution until the resultant solution pH is in the range of about pH 7.9 to about 8.1 following the procedure in step 2) of Example 2 above.

c) A strip of filter paper, e.g., No. 204 from Eaton-Dikeman Scientific Specialties, Co. of Mt. Holly Springs, Pa., U.S.A., is immersed in the partially neutralized solution from the previous step, removed, and subsequently dried.

d) The dried polymer-bearing strip is then immersed in a solution comprising 1.2 grams of bromothymol blue per liter of methanol, removed, and subsequently dried.

e) A piece of the resultant treated filter paper is cut into a rectangular form having dimensions of 0.5 cm×2 cm and is adhesively affixed to a 1.0 mil polypropylene film, such as is currently available as X15306 from Tredegar Industries of Terre Haute, Ind., U.S.A.

f) The filter-paper side of the resultant composite is affixed along its perimeter to the garment-facing side of a disposable diaper topsheet in the crotch or urine loading region of the product.

Example 4

A wearable article having a qualitative dehydration indicator may be constructed as follows:

a) A urinalysis test strip adapted to provide an indication of urine specific gravity via measurement of the ionic strength of the urine is provided. A suitable currently available urinalysis test strip is the CHEMSTRIP™ 10 urinalysis strip available from Roche Diagnostics of Indianapolis, Ind., U.S.A. The "specific gravity" measuring section of the urinalysis test strip containing a urine ionic strength indicating composition, such as ethyleneglycol-bis[aminoethyl ether] tetraacetic acid and bromothymol blue, is cut from the test strip.

b) The cut segment from a) is adhesively affixed to the garment-facing side of a disposable diaper topsheet in the crotch or urine loading region of the product, oriented such that the reagent-containing side is facing the topsheet. Care is taken to avoid covering the entire surface of the reagent strips segment with adhesive to allow urine to contact the strip and provide a signal. In the case of the CHEMSTRIP™ 10 urinalysis strip, when the color changes to tan, the urine specific gravity is approximately 1.030, indicating a condition of severe dehydration. In the case of other test strips, the manufacturer's instructions for reading the color signal for a given test strip should be followed.

What is claimed is:

1. A disposable absorbent article or receiving and containing bodily exudates including urine from a wearer, the disposable absorbent article comprising;
    an outer cover adapted to fit about a portion of the wearer;
    a fluid permeable topsheet onto and through which the urine is received;
    an absorbent structure disposed adjacent at least a portion of the outer cover; and
    a dehydration indicator adapted to measure a urine ionic strength correlated to a specific gravity of the wearer's urine and provide a visible signal when the urine ionic strength reaches a value corresponding to a predetermined threshold of the specific gravity, the dehydration indicator comprising a chemical indicating composition providing a visible signal indicative of a level of dehydration in response to an ionic strength of urine exuded into the disposable absorbent article by a wearer, wherein the chemical indicating composition is covered on a wearer-facing surface by a semipermeable membrane formed of cellulose acetate, cellulose diacetate, cellulose triacetate, agar acetate, beta glucan acetate, polymeric epoxides, semipermeable polyurethanes, or semipermeable polyglycolic acid.

2. The absorbent article of claim 1 wherein the dehydration indicator provides a qualitative indication of a urine specific gravity associated with dehydration.

3. The absorbent article of claim 1 wherein the dehydration indicator comprises an indicium.

4. The absorbent article of claim 3 wherein the indicium serves as a color key for the dehydration indicator signal.

5. The disposable absorbent article of claim 1 wherein the dehydration indicator is disposed on at least a portion of the topsheet.

6. The disposable absorbent article of claim 5 wherein the dehydration indicator is detachable from the topsheet.

7. The disposable absorbent of claim 1 further comprising a translucent cover covering the dehydration indicator.

8. The disposable absorbent article of claim 1 wherein the dehydration indicator is disposed on a carrier element.

9. The disposable absorbent article of claim 1 additionally comprising a fluid transport element in fluid communication with the dehydration indicator and serving to transport urine to the dehydration indicator.

* * * * *

UNITED STATES PATENT AND TRADEMARK OFFICE
CERTIFICATE OF CORRECTION

| | | |
|---|---|---|
| PATENT NO. | : 8,217,217 B2 | |
| APPLICATION NO. | : 12/043979 | |
| DATED | : July 10, 2012 | |
| INVENTOR(S) | : Joseph Raymodn Diehl et al. | |

It is certified that error appears in the above-identified patent and that said Letters Patent is hereby corrected as shown below:

<u>Column 12</u>
Line 22, delete "or" and insert --for--.

Signed and Sealed this
Eleventh Day of September, 2012

David J. Kappos
*Director of the United States Patent and Trademark Office*